United States Patent
Garner et al.

(10) Patent No.: US 9,427,170 B2
(45) Date of Patent: Aug. 30, 2016

(54) DEVICE AND METHOD FOR DETECTION OF ATRIAL FIBRILLATION

(71) Applicant: Biotronik SE & Co. KG, Berlin (DE)

(72) Inventors: Garth Garner, Tigard, OR (US); R. Hollis Whittington, Portland, OR (US); Dirk Muessig, West Linn, OR (US)

(73) Assignee: BIOTRONIK SE & CO. KG, Berlin (DE)

( * ) Notice: Subject to any disclaimer, the term of this patent is extended or adjusted under 35 U.S.C. 154(b) by 0 days.

(21) Appl. No.: 14/631,292

(22) Filed: Feb. 25, 2015

(65) Prior Publication Data

US 2015/0245779 A1 Sep. 3, 2015

Related U.S. Application Data

(60) Provisional application No. 61/946,909, filed on Mar. 3, 2014.

(51) Int. Cl.
| | |
|---|---|
| *A61B 5/02* | (2006.01) |
| *A61B 5/046* | (2006.01) |
| *A61B 5/00* | (2006.01) |
| *A61B 5/042* | (2006.01) |

(52) U.S. Cl.
CPC .............. *A61B 5/046* (2013.01); *A61B 5/6869* (2013.01); *A61B 5/7203* (2013.01); *A61B 5/7221* (2013.01); *A61B 5/042* (2013.01)

(58) Field of Classification Search
USPC .................................. 600/509, 516
See application file for complete search history.

(56) References Cited

U.S. PATENT DOCUMENTS

| | | | |
|---|---|---|---|
| 5,304,139 A | 4/1994 | Adams et al. | |
| 6,434,426 B1 | 8/2002 | Munneke et al. | |
| 2010/0099996 A1 | 4/2010 | Nigam et al. | |
| 2010/0312131 A1 | 12/2010 | Naware et al. | |
| 2012/0203123 A1* | 8/2012 | Mahajan | A61B 5/024 600/509 |

OTHER PUBLICATIONS

European Search Report received from EP Application Serial No. 15156488.7-1657, dated Jul. 22, 2015, 6 pages.

* cited by examiner

*Primary Examiner* — Nicole F Lavert
(74) *Attorney, Agent, or Firm* — ARC IP Law, PC; Joseph J. Mayo

(57) ABSTRACT

A cardiac device and method thereof for detecting atrial fibrillation within a mean heart signal of a body, wherein the cardiac device includes at least two sensing electrodes. The method includes providing an input heart signal, detecting sense events (VS) and noise events (VN), and generating further noise events (VN) each at a predetermined time interval after a noise event (VN) has been detected and when the noise event (VN) continues. The method includes incrementing a noise counter for each noise event (VN) and each further noise event (VN), and terminating the detection of atrial fibrillation when the noise counter reaches a predetermined limit.

13 Claims, 7 Drawing Sheets

DEVICE AND METHOD FOR DETECTION OF ATRIAL FIBRILLATION

This application claims the benefit of U.S. Provisional Patent Application 61/946,909 filed on 3 Mar. 2014, the specification of which is hereby incorporated herein by reference.

BACKGROUND OF THE INVENTION

1. Field of the Invention

Embodiments of the invention generally relate to an apparatus and a method for detection of atrial fibrillation within a mean heart signal of a body.

2. Description of the Related Art

Generally, implantable cardiac monitors are implantable medical devices that monitor the electrical activity of the heart by using electrodes in contact with the body tissue. These electrodes are usually located at the case of the implanted medical device that is implanted under the skin of the chest close in vicinity of the heart. Alternatively the electrodes are typically located at the distal end of at least one subcutaneous implanted electrode line connected to the implantable cardiac monitor. Implantable cardiac stimulators such as pacemakers, defibrillators and cardiac resynchronization devices, generally employ electrodes located at the distal end of electrode lines that are implanted in the heart chambers and connected to the implanted device and may also provide the functionality of an implantable cardiac monitor. Cardiac events are typically detected by analyzing the electrical activity of the heart, e.g. by detecting cardiac intervals, for example, but not limited to the QRS complex. Generally, from the time intervals between detected QRS complexes, the heart rate may be derived. Typically, additional diagnostic information may be derived from the characteristics of the cardiac interval or the QRS complex.

Atrial fibrillation (AF) is generally an abnormal high heart rate originating from the atrium of the heart. Implantable cardiac monitors may typically detect AF and store snapshots of cardiac activity before and during detected AF for further analysis. Stored snapshots and other data of the implantable cardiac monitor may generally be transmitted using short range (inductive) or long range (RF) telemetry to devices external to the body, to remote devices or central servers for further analysis.

Generally, detection of cardiac activity may have interference due to noise. Signals with interference by noise may typically be misinterpreted as cardiac activity, e.g. a noise portion may be misinterpreted as QRS complex, leading to false AF detections. These false AF detections are generally due to the irregular nature of false QRS detections arising from noise at the electrodes. In such cases, the implantable cardiac monitor may generally present snapshots of cardiac events that show frequent examples of atrial fibrillation (AF) snapshots due to noise, when AF is not present.

Typically, during AF detection, the AF detection attempts to terminate within a confirmation period after detection of AF. Generally, if AF detection is not terminated by the end of the confirmation period, AF is declared and an AF snapshot is stored. The AF detection will typically terminate once a programmed number of consecutive intervals packets are found to be stable. Sometimes during a high noise presence, noise is generally misclassified as QRS detections rather than as noise. Typically, these misclassifications may lead to false unstable intervals. These unstable intervals generally don't allow AF detection to terminate and therefore lead to AF confirmation, which, results in AF confirmations that show a large amount of noise detections in the snapshots. Generally, AF detection in known devices ignores intervals with noise and removes such intervals from consideration of AF detection or termination.

AF snapshots that show a high presence of noise and no clear AF detection typically do not offer any clinical advantage to the patient. In addition, generally, these snapshots may cause mistrust of the device classification of AF.

Such false AF snapshots are not desired. Therefore, in view of the above, there is a need for an improved device and method to detect atrial fibrillation.

BRIEF SUMMARY OF THE INVENTION

One or more embodiments of the invention provide an apparatus and a method to detect atrial fibrillation signals within a heart signal of a body. In at least one embodiment, the apparatus, such as a cardiac device, includes at least two sensing electrodes, means for providing an input heart signal, for example at least one input channel, and means for detecting sense events (VS) and noise events (VN), for example a detector or sensor. According to one or more embodiments, the apparatus may include a noise counter, and means for terminating the detection of atrial fibrillation when the noise counter reaches a predetermined limit, for example via logic residing within a computer processor, otherwise referred to herein as a "processor". In one or more embodiments of the invention, in the context of the disclosure presented herein, a noise event is not a QRS event.

In at least one embodiment of the invention, the cardiac device may include means for generating further noise events (VN), for example at least one noise marker generator, each at a predetermined time interval after a noise event (VN) has been detected and when the noise event (VN) continues. In one or more embodiments, the apparatus may include means for incrementing and resetting the noise counter for each noise event (VN) and each further noise event (VN), for example via the processor.

In at least one embodiment of the invention, the cardiac device may include one or more of an interval counter, means for incrementing, decrementing and resetting the interval counter, for example via the processor, a stable packet counter, and means for incrementing and decrementing the stable packet counter, for example via the processor. In one or more embodiments, for a noise event (VN), the interval counter is decrementable and the noise counter is incrementable, wherein the noise counter and the interval counter are resettable. In at least one embodiment, for a noise event (VN), a stable packet counter is incrementable when the noise counter reaches a predetermined limit, wherein the detection of atrial fibrillation is terminated when the stable packet counter reaches a predetermined limit.

When the noise counter reaches a predetermined limit, according to one or more embodiments of the invention, then the noise counter is reset to zero and the stable packet counter is incremented. When the stable packet counter reaches a predetermined limit, then AF is terminated.

The advantage of the apparatus according to at least one embodiment of the invention is that the detection of atrial fibrillation (AF) may be terminated quickly and reliably. In one or more embodiments, the termination is based on a certain number of detected or generated noise events. In at least one embodiment, the number of noise events may be chosen between two and twenty-four, such as between two and eight or such as four.

The apparatus, according to at least one embodiment of the invention, does not impact AF detection directly; it affects termination of AF detection and allows the AF detection to be terminated in the presence of noise detected as VN events. Hence, in one or more embodiments, the apparatus may be designated as a control or termination apparatus for AF detection.

In at least one embodiment of the invention, for a sense event (VS), the interval counter is incrementable for two consecutive sense events (VS), wherein the noise counter and the interval counter are resettable. In one or more embodiments, for a sense event (VS), the stable packet counter is incrementable when the interval counter reaches a defined packet size and meets a stability threshold, wherein the detection of atrial fibrillation is terminated when the stable packet counter reaches a predetermined limit.

By way of at least one embodiment, for a noise event, an interval counter may be decremented and the noise counter may be incremented, wherein the noise counter and the interval counter may be reset. In one or more embodiments, for a noise event, a stable packet counter may be incremented when the noise counter reaches a predetermined limit, wherein the detection of atrial fibrillation may be terminated when the stable packet counter reaches a predetermined limit. According to at least one embodiment of the invention, a packet is defined by a number of consecutive intervals, such as eight to sixty-four intervals or such as sixteen intervals. In one or more embodiments, an interval or ventricular interval may be defined by two consecutive events of the input heart signal. In at least one embodiment, the packet is considered stable when a pre-specified number of intervals in the packet are within a programmable percentage of the mean interval. In one or more embodiments, the number of stable intervals may be 5 within a programmable percentage of 12.5%. The stable packet counter may already be implemented in the cardiac devices and may be utilized, according to at least one embodiment of the invention, in a different manner. For example, in at least one embodiment, the stable packet counter may be incremented not by stable packets but by noise events. In one or more embodiments, the noise events may increment the stable packet counter when a predetermined limit is reached. According to at least one embodiment of the invention, the stable packet counter may be designated and used as a noise packet hysteresis. In one or more embodiments, a noise threshold of the noise counter may be in the range of two to forty-eight, such as four. In at least one embodiment, the noise packet hysteresis may be in the range of one to eight, such as one.

According to one or more embodiments, the noise counter may be incremented only when a noise window is active. In at least one embodiment, such implementation may improve noise handling and may improve detection of single noise events. In one or more embodiments, the noise window is a predefined duration that starts when the AF detection algorithm detects AF. In at least one embodiment, noise detection is active during the noise window. In one or more embodiments, the noise window may be anywhere between 30 seconds, the length of the AF confirmation period or longer, such as 1 minute.

By way of at least one embodiment of the invention, the noise counter and the interval counter are resettable and the stable packet counter is incrementable only when a number of unstable intervals are below a predetermined limit.

In one or more embodiments, for a sense event, an interval counter may be incremented for two consecutive sense events, wherein the noise counter and the interval counter may be reset. In at least one embodiment, for a sense event, a stable packet counter may be incremented when the interval counter reaches a defined packet size, wherein the detection of atrial fibrillation may be terminated when the stable packet counter reaches a predetermined limit.

In one or more embodiments, a sense event (VS) is detectable for a QRS event in the input heart signal.

In at least one embodiment of the invention, the noise counter and the interval counter may be reset and the stable packet may be incremented only when a number of unstable intervals are below a predetermined limit. According to one or more embodiments, such provision serves as a control function eliminating processing of VS events for too many unstable intervals. In at least one embodiment, the programmed limit for unstable intervals may be between one to sixteen.

In one or more embodiments, a sense event may be detected for a QRS event in the input heart signal. In at least one embodiment, a clean undistorted QRS event is classified as a sense event or ventricular sense (VS).

By way of one or more embodiments of the invention, the predetermined time interval for incrementing the noise counter due to an ongoing noise period may include a range between 0.5 to 4 seconds, such as 2 seconds. According to at least one embodiment, such timings have shown the best results for most applications.

In one or more embodiments, the generation of further noise events may be only executed during a programmable duration of time following a detection of atrial fibrillation. According to at least one embodiment, such noise behavior being only active for a programmable duration following an AF detection may avoid short bursts of noise terminating the AF detection in presence of real AF.

In one or more embodiments of the invention, a ventricular interval may be defined by two consecutive VS events of the input heart signal, and the cardiac device may start detecting AF when at least one of the following conditions is met: a) the rate of ventricular intervals is above a predetermined rate limit and b) a predetermined number of ventricular intervals is determined to be not stable. In at least one embodiment, both conditions may be combined.

BRIEF DESCRIPTION OF THE DRAWINGS

The above and other aspects, features and advantages of at least one embodiment of the invention will be more apparent from the following more particular description thereof, presented in conjunction with the following drawings, wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1A:
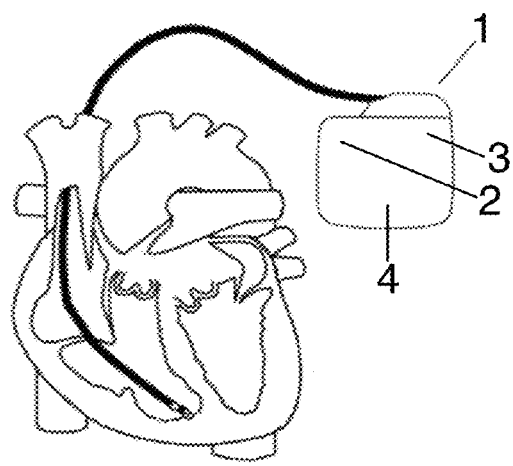
FIG. 1A shows an embodiment of a cardiac device according to the invention.
Figure 1B:
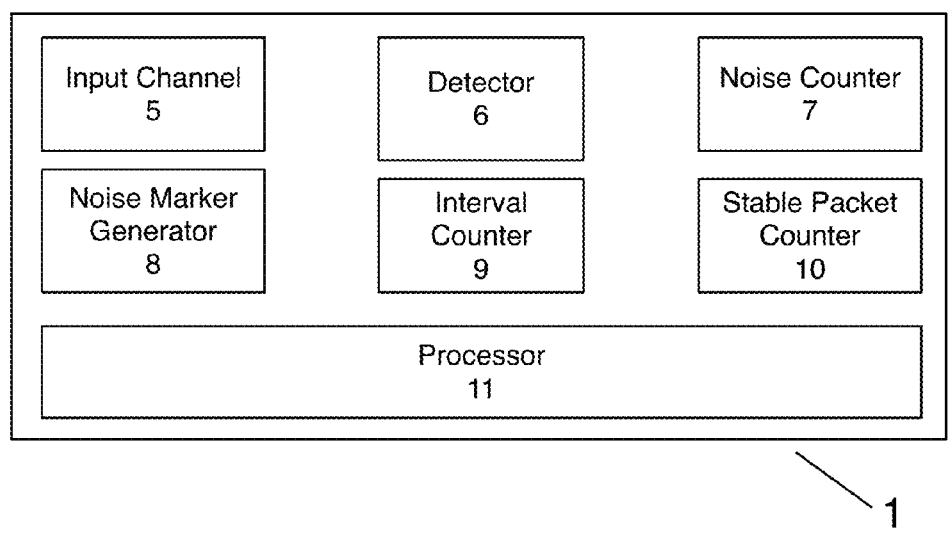
FIG. 1B shows an overall schematic of the cardiac device according to at least one embodiment of the invention.

FIG. 1A and FIG. 1B show schematics of a cardiac device 1, such as an atrial fibrillation (AF) detection device, according to at least one embodiment of the invention. In at least one embodiment, the cardiac device 1 is an implantable cardiac monitor that monitors the electrical activity of the heart by using electrodes in contact with the body tissue. In one or more embodiments, the cardiac device 1 may include three sensing electrodes 2, 3 and 4, which are positioned within a housing of the cardiac device 1.

As shown in FIG. 1B, by way of one or more embodiments, the cardiac device 1 may include one or more of at least one input channel 5, a detector or sensor 6 that detects sense events (VS) and noise events (VN), a noise counter 7, and a noise marker generator 8 that generates further noise events (VN), an interval counter 9 and a processor 11. In at least one embodiment the processor 11 may terminate the detection of atrial fibrillation when the noise counter 7 reaches a predetermined limit. In one or more embodiments, the processor may increment and reset the noise counter for each noise event (VN) and each further noise event (VN). In at least one embodiment of the invention, the processor may increment decrement and reset the interval counter 9, and may increment and decrement the stable packet counter 10.

The cardiac device 1, according to at least one embodiment, may include at least one input channel 5, for example three input channels, that receive different projections of the heart signal as input heart signals. In one or more embodiments, each input channel may use a single pair of the three sensing electrodes 2, 3 and 4 and each input channel 5 may sense a different planar projection of the heart signal, wherein the projections are coincident in time. In at least one embodiment, noise on each input channel may be determined, in part, by the local activity around the sensing electrodes 2, 3 and 4 in that particular pair. By way of one or more embodiments, combining the three input channels into a single input channel may increase the signal to noise ratio by smoothing some of the random noise associated with each input channel, while emphasizing the QRS-signals or QRS complexes.

The following disclosure refers to a single input channel and a single signal, respectively as well as to a combined input channel and a combined signal, respectively, according to at least one embodiment. One or more embodiments of the invention relates to single and combined signals.

In at least one embodiment, the cardiac device 1 monitors the electrocardiogram (ECG) for QRS events. In one or more embodiments, when the ECG signal exceeds a threshold, then a QRS may be detected. In at least one embodiment, the cardiac device 1 may then look for a period of time and then classify the QRS detection as VS (ventricular sense) or VN (ventricular noise). In one or more embodiments, the cardiac device 1 may monitor ventricular intervals (two consecutive VS events). If the cardiac device 1 determines the intervals as unstable, according to at least one embodiment, then it classifies the rhythm as AF. After AF classification, in one or more embodiments of the invention, the cardiac device 1 may attempt to terminate AF detection. In at least one embodiment, AF detection is terminated if the ventricular intervals are classified as stable. If AF detection is unable to terminate before the end of the confirmation time, in one or more embodiments, a snapshot may be stored.

In at least one embodiment of the invention, the AF detection of the cardiac device 1 addresses false AF snapshots that were due to noise by counting VN events starting when AF is detected and continuing to count VN events for a programmable duration. In one or more embodiments, the apparatus may carry out the steps of incrementing a noise counter 7 for each VN event and each further VN event. When the noise counter 7 reaches a predetermined limit, according to at least one embodiment, then the noise counter 7 may be reset to zero and the stable packet counter 10 may be incremented. When the stable packet counter 10 reaches a predetermined limit, according to at least one embodiment, then AF may be terminated. In one or more embodiments, if the cardiac device 1 has ongoing noise detections, a VN may be generated every two seconds. In at least one embodiment of the invention, such noise modifications make the detection more likely to terminate in the presence of noise than to declare AF. In one or more embodiments, the noise behavior may only be active for a programmable duration following AF detection to avoid short bursts of noise terminating real AF.

Figure 2:
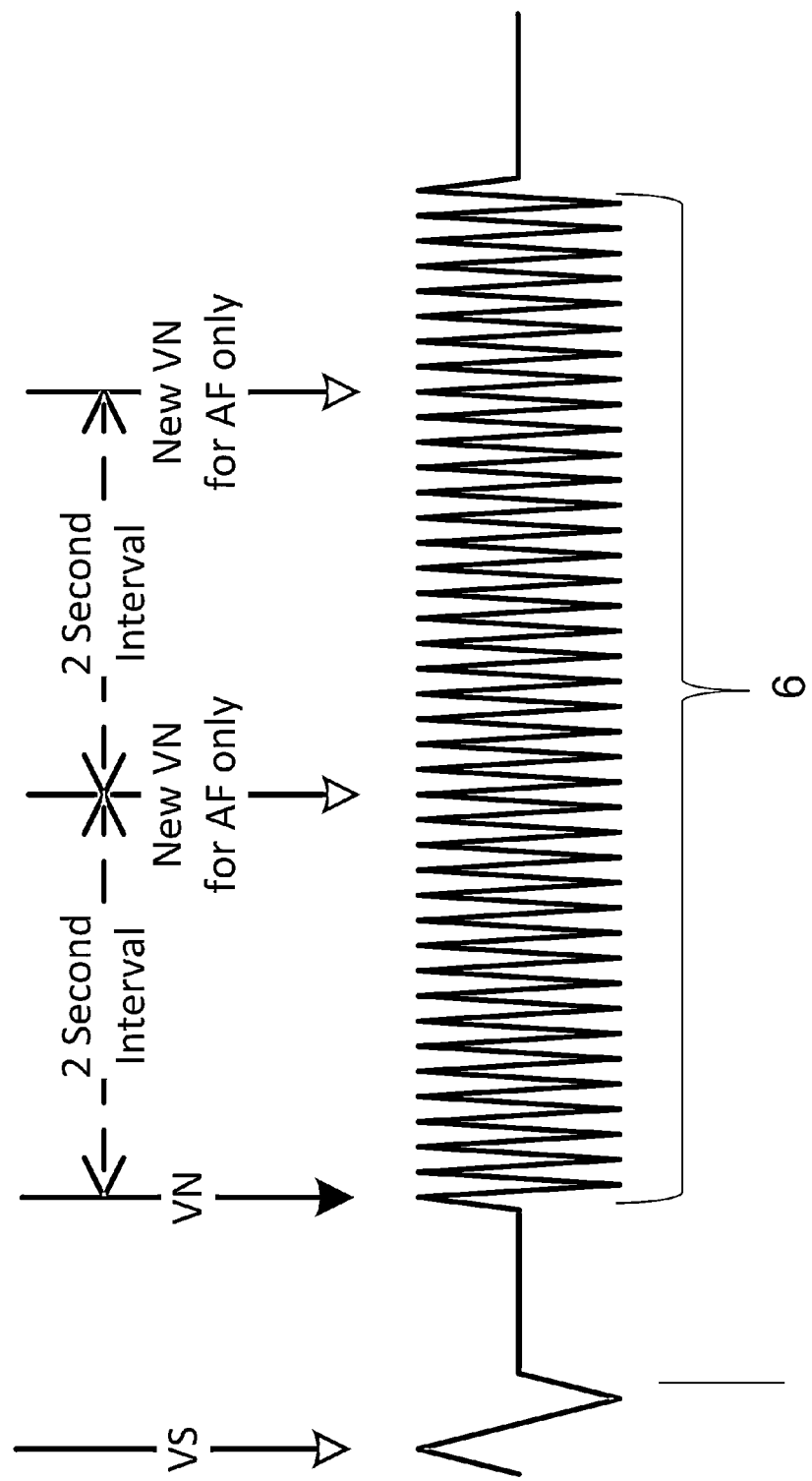
FIG. 2 shows a detection scheme for a schematic signal representing a measured heart signal of a body according to at least one embodiment of the invention.

FIG. 2 shows an exemplary signal plot or signal waveform as detected by the cardiac device 1, according to at least one embodiment of the invention. The signal plot shows the last part of a QRS complex 5 followed by burst of noise 6, according to one or more embodiments. Clinical snapshots have shown signals with persistent noise where only one VN event was classified, due to the nature of the hardware. In at least one embodiment of the invention, the AF detection may check every two seconds to see if the device has ongoing noise. In one or more embodiments, if the cardiac device 1 has ongoing noise for two seconds, then a new VN (ventricular noise) event is classified and passed on to the AF detection. In at least one embodiment, all events may be annotated with a downward pointing arrow with text. The first event in FIG. 2 is a VS (ventricular sense) event and is annotated with a downward facing arrow with "VS" text. The second event in FIG. 2 is a VN event and is annotated with a downward facing arrow with "VN" text. Both of these events are used by the AF detection according to at least one embodiment of the invention.

The third and fourth events in FIG. 2 are annotated with downward pointing arrows with "New VN for AF only" text. The third and fourth VN events are newly introduced and used by the AF detection device, according to at least one embodiment of the invention.

FIG. 2 shows a five second burst of noise 6, according to one or more embodiments of the invention. A typical AF detection would process one VN event, while the AF detection herein according to at least one embodiment of the invention processes three consecutive VN events. The three VN events, in one or more embodiments, are spaced apart by a two second interval. In at least one embodiment, the duration of the interval may be differently chosen, such as between 0.5 to 4 seconds and such as between 1 and 3 seconds.

Figure 3:
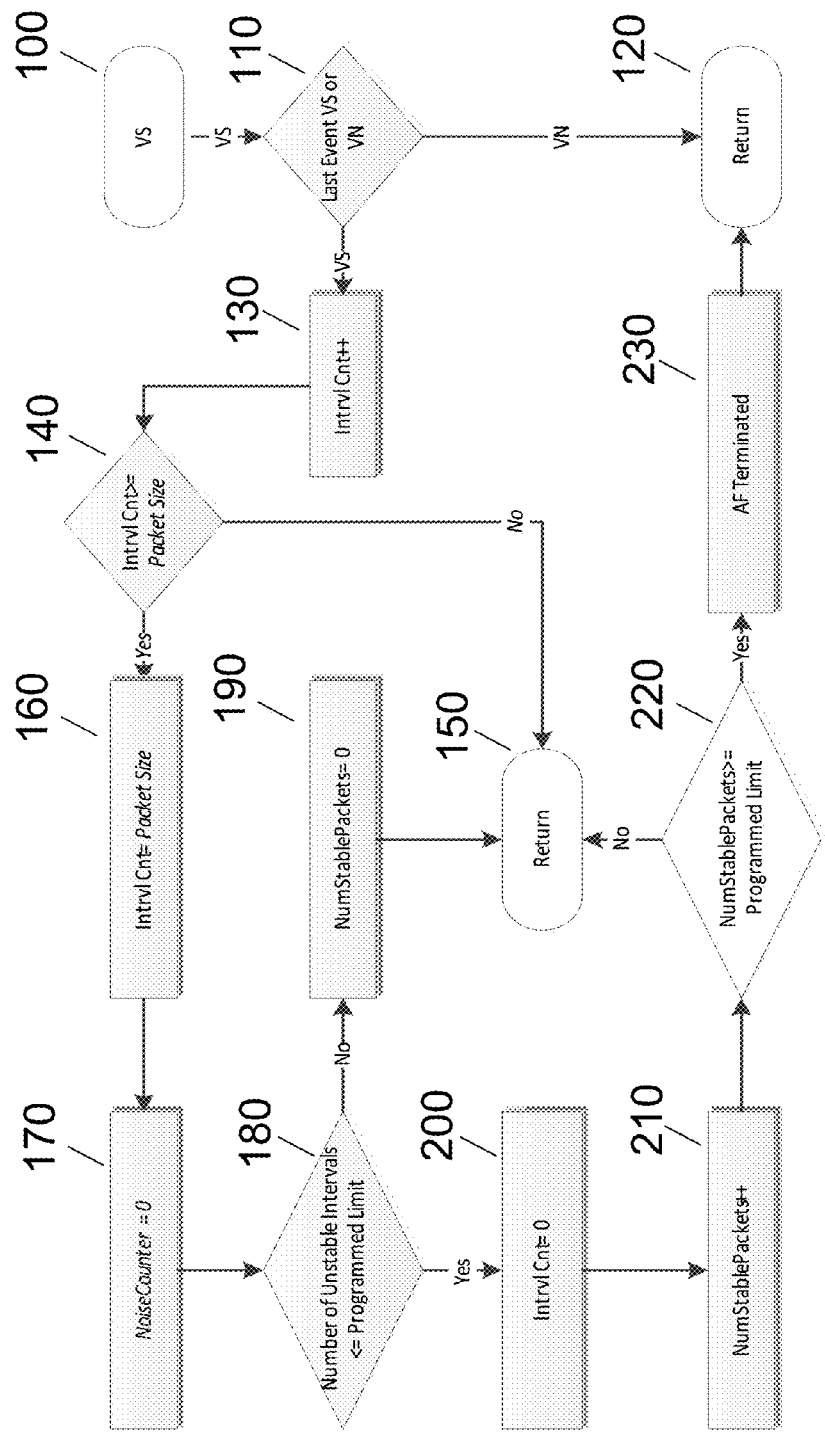
FIG. 3 shows a schematic illustration of the general AF detection flow for a sense event according to at least one embodiment of the invention.

FIG. 3 shows an AF detection flow for a sense event according to at least one embodiment of the invention.

Figure 4:
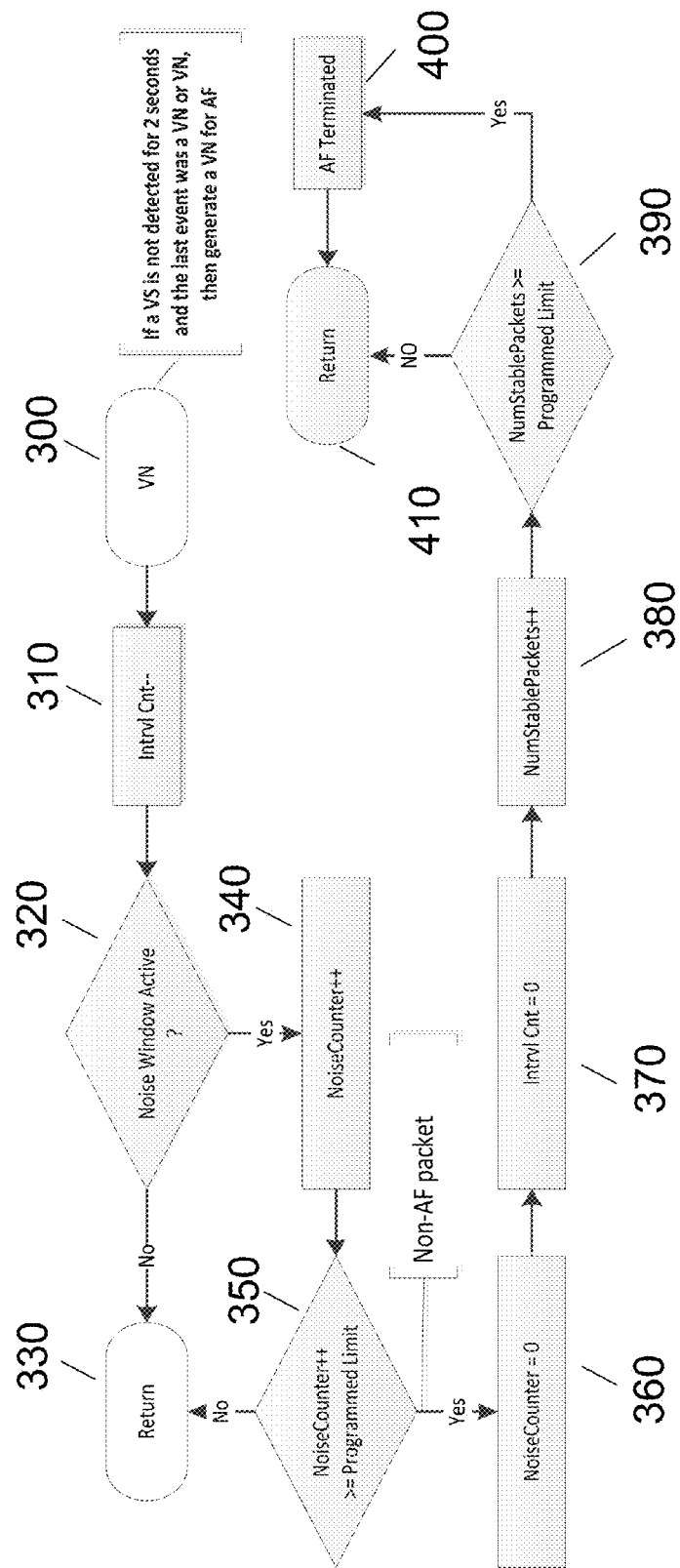
FIG. 4 shows a schematic illustration of the general AF detection flow for a noise event according to at least one embodiment of the invention.

AF noise detection according to at least one embodiment of the invention includes VS (QRS detections) and VN (QRS detections classified as noise) event handling as shown in FIG. 3 and FIG. 4. In one or more embodiments, the detection starts at the VS box or VN box in FIG. 3 and FIG. 4, respectively. In at least one embodiment, the detection terminates at the return boxes in FIG. 3 and FIG. 4.

By way of one or more embodiments, the AF detection performs different actions depending on the event type (VS or VN). In at least one embodiment, the portion of the detection that is used when a VS is classified is shown in FIG. 3. When a VS arrives, in one or more embodiments, the detection device processes the VS, starting in block 100. In block 110, in at least one embodiment, it is checked whether the last or previous event was a VS or a VN event. In one or more embodiments, in case of a prior VN event, the detection device terminates at block 120 and returns to a monitoring or detection mode. In at least one embodiment, in case of a prior VS event the detection device branches to block 130 where an interval counter is increased or incremented. In one or more embodiments, the interval counter may be incremented when two consecutive VS events are detected.

At block 140, in at least one embodiment of the invention, the interval counter is compared to a packet size. In one or more embodiments, the packet size corresponds to a defined number of intervals. For example, in at least one embodiment, 16 intervals define a packet. In one or more embodiments, the number of intervals per packet may be in the range of 8 to 64.

According to at least one embodiment, for an interval count lower than the packet size the detection device terminates at block 150 and returns to a monitoring or detection mode. In one or more embodiments, upon arrival of a VS that completes a packet (Intrvl Cnt=Packet Size) in block 160, the noise counter is reset to zero in block 170. In at least one embodiment, the noise counter counts noise or VN events and may be incremented each time a VN event is detected.

In a next step or at block 180, in one or more embodiments, a check is performed whether the number of unstable intervals is smaller than or as equals to a programmed limit. By way of at least one embodiment, if that is not the case, i.e. if the number of unstable intervals exceeds a programmed limit, the counter of stable packets NumstablePackets is reset to zero in step 190 and the detection device terminates at block 150.

In one or more embodiments, for a number of unstable intervals smaller than or as equal to the programmed limit, the detection device branches to block 200. At block 200, in at least one embodiment of the invention, the interval counter 9 is reset as the packet size is reached and the next packet continues.

In one or more embodiments, in block 210, the counter of stable packets NumstablePackets is incremented as a stable packet has been detected. In block 220, in at least one embodiment, the counter of stable packets NumstablePackets is checked against a programmed limit, which may be designated as AF packet hysteresis. In one or more embodiments, if the counter of stable packets NumstablePackets is smaller than the AF packet hysteresis, the detection device branches to block 150 where it terminates or exits this routine. In one or more embodiments, if the counter of stable packets NumstablePackets is larger than or as equal to the AF packet hysteresis, the detection device branches to block 230 where the AF detection is terminated. In at least one embodiment, after termination of the AF detection the detection device returns to block 120.

One or more embodiments of the invention as shown in FIGS. 3 and 4 do not impact AF detection itself. The routines as shown in FIGS. 3 and 4 according to one or more embodiments, only affect termination of the AF detection and allow the AF detection to terminate in the presence of noise detected as VN events. The disclosure presented herein of FIG. 3 and FIG. 4 apply to the termination phase of the AF detection, according to at least one embodiment of the invention.

In one or more embodiments, the portion of the detection or the detection that is used when a VN is classified is shown in FIG. 4. FIG. 4 shows the introduction of the noise detection and how it interacts with the existing AF detection termination phase, according to at least one embodiment of the invention, which starts at the block VN 300.

When a VN is received, in at least one embodiment, the interval counter Intrvl Cnt is decremented in block 310. In block 320, in one or more embodiments, it is checked whether the noise window is active. In at least one embodiment, when no noise window is active, the detection terminates at block 330 and returns to a monitoring or detection mode.

By way of one or more embodiments, if the noise window is active, the noise counter NoiseCounter is incremented in block 340. In at least one embodiment, if the noise counter exceeds a threshold (block 350), the noise counter is reset in block 360. In one or more embodiments, if the noise counter does not exceed a threshold (block 350) the detection terminates at block 330 and returns to a monitoring or detection mode.

In block 370 the interval counter Intrvl Cnt is reset to zero and in block 380 the number of stable packets is incremented, encouraging the device to terminate AF, according to one or more embodiments of the invention. As long as the programmed threshold of stable packets is not reached (block 390), in at least one embodiment, the detection device terminates (block 410) and returns to a monitoring or detection mode. In one or more embodiments, when the programmed threshold of stable packets is reached (block 390), AF is terminated in block 400. In at least one embodiment, the programmed threshold of stable packets may be designated as the noise packet hysteresis. In one or more embodiments, in block 410, the detection device terminates and returns to a monitoring or detection mode.

At least one embodiment of the invention may use the additional VN events or counts to artificially increase the number of stable packets so as to terminate the AF detection. In one or more embodiments, for ongoing noise, i.e. successive VN events, the detection is therefore independent of a certain number of stable packets or intervals which otherwise need to be detected.

Figure 5:
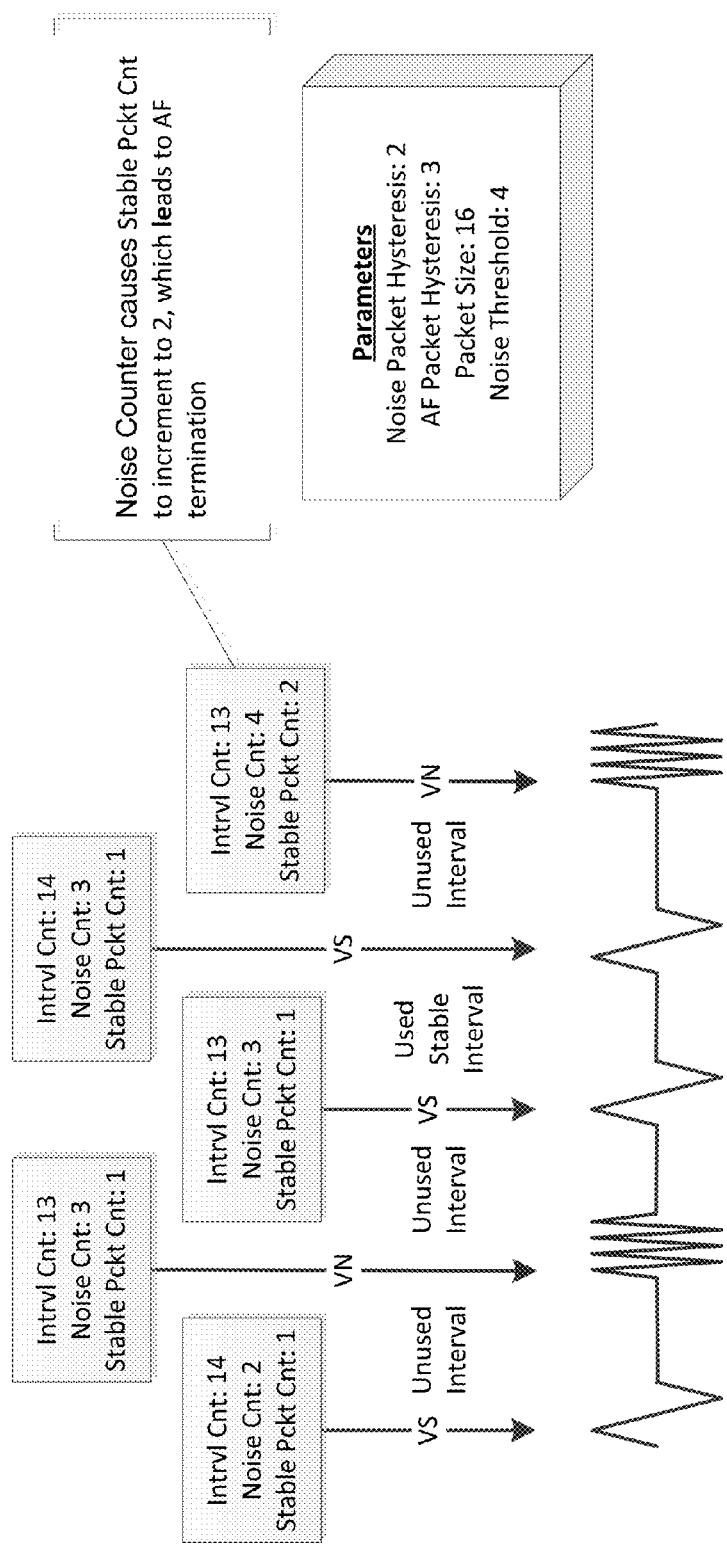
FIG. 5 shows a schematic operational sequence according to at least one embodiment of the invention in which a noise counter leads to AF termination.
Figure 6:
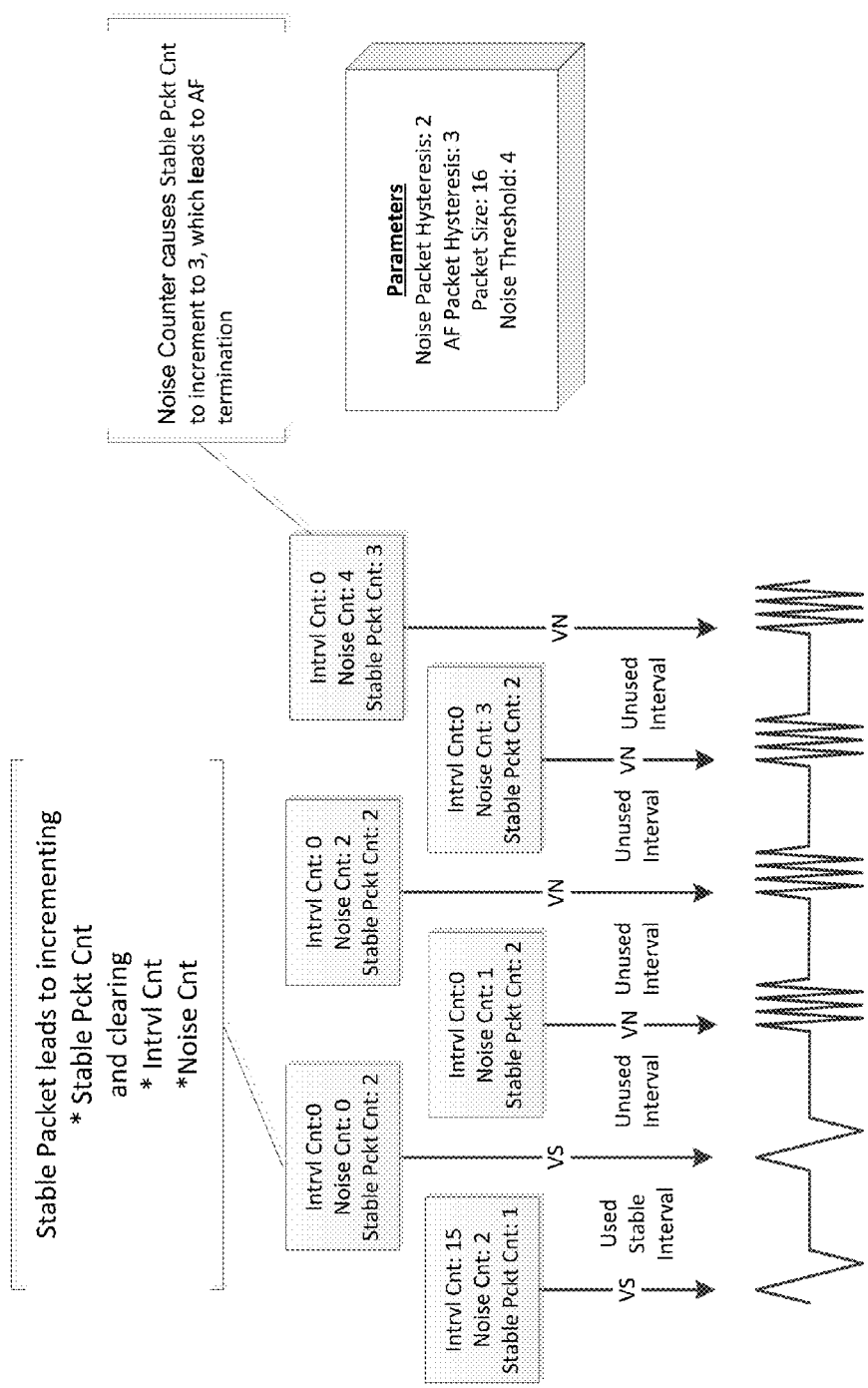
FIG. 6 shows a schematic operational sequence according to at least one embodiment of the invention in which the noise counter leads to AF termination for a stable (non-AF) packet.
Figure 7:
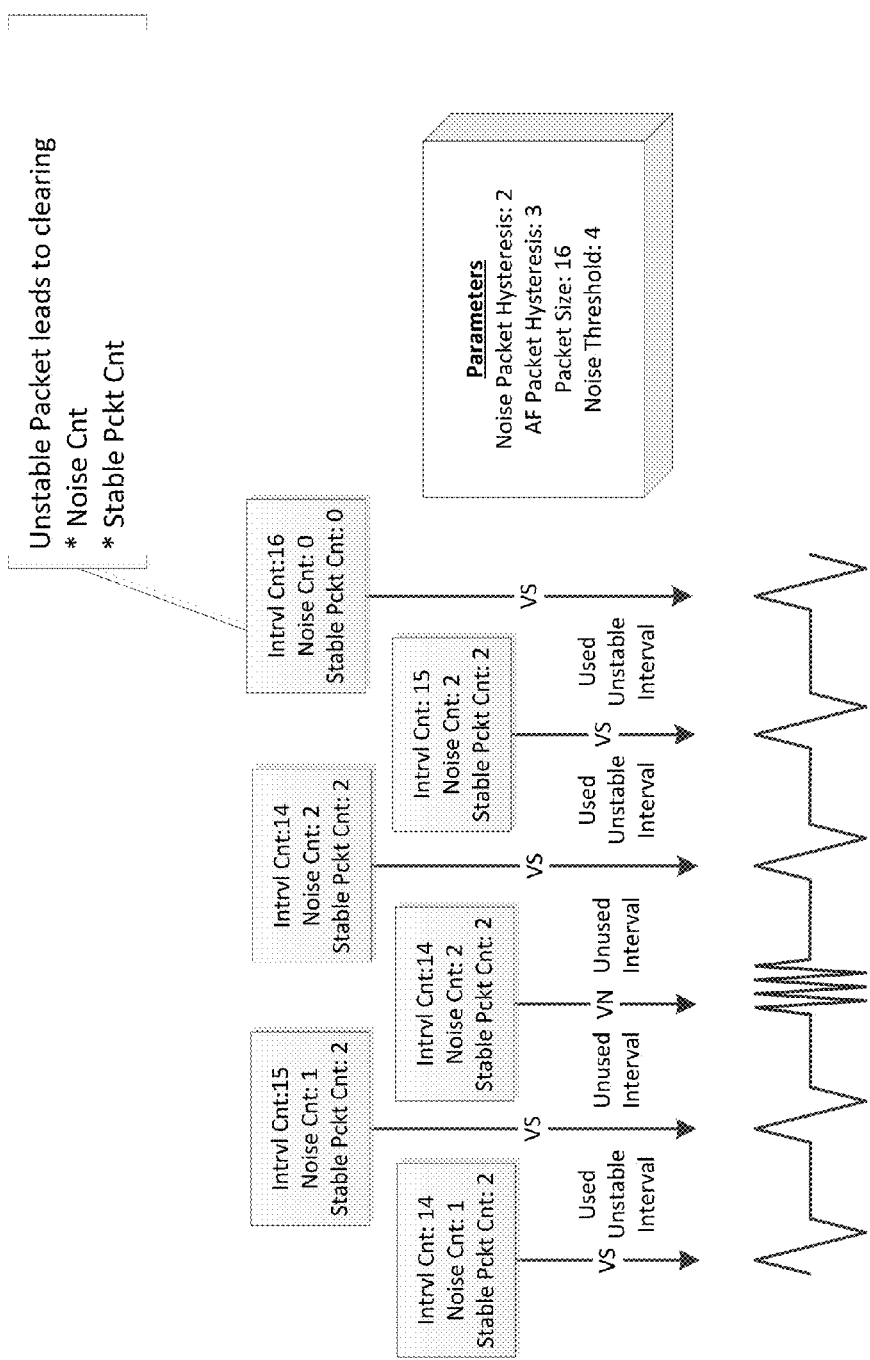
FIG. 7 shows a schematic operational sequence according to at least one embodiment of the invention in which an unstable (AF) packet leads to clearing a noise count.

FIGS. 5 to 7 show examples to illustrate the AF detection behavior according to at least one embodiment of the invention. In all of the examples shown in FIGS. 5 to 7, the parameters are the same and shown in the bottom right corner. In one or more embodiments, the term "AF termination" in FIG. 5 and FIG. 6 refers to AF detection termination as described above. In at least one embodiment, AF detection terminates when it counts a programmable number of consecutive stable packets. When VN events reach the noise threshold, in one or more embodiments, then the same stable packet counter is incremented. On VS, as shown in FIG. 3, in at least one embodiment, when the stable packet counter is incremented, it is compared to the AF packet hysteresis. On VN, as shown in FIG. 4, in one or more embodiments, when the stable packet counter is incremented, it is compared to the noise packet hysteresis. In at least one embodiment, if the stable packet counter is greater than or equal to either of these thresholds or hysteresis, as previously described, the AF detection is terminated. In one or more embodiments, as shown in FIGS. 5 to 7, each VS event is handled according to the detection shown in FIG. 3 while each VN event is handled according to the detection shown in FIG. 4.

In the example shown in FIG. 5, according to at least one embodiment, the interval count (Intrvl Cnt) starts at 14. On VN events, in one or more embodiments, the counter is decremented. On VS events that conclude a used interval, in at least one embodiment, the counter is incremented (fourth event of FIG. 5). In one or more embodiments, on the last VN event (fifth event of FIG. 5), the Noise Count (Noise Cnt) reaches the noise threshold and the stable packet count (Stable Pckt Cnt) is incremented. When the stable packet count is incremented, in at least one embodiment, it reaches the Noise Packet Hysteresis value (block 390 in FIG. 4) and therefore the AF detection is terminated.

In the example shown in FIG. 6, in one or more embodiments of the invention, the interval count (Intrvl Cnt) starts at 15. On the next VS event, in at least one embodiment, there are enough intervals for the AF detection device to check for stability. As such, in one or more embodiments, the AF detection device may find the packet stable, such that the stable packet count (Stable Pckt Cnt) is incremented and the noise count and the interval count are cleared. The next four VN events lead to incrementing the stable packet count according to at least one embodiment of the invention. In one or more embodiments, when the stable packet count is incremented, the stable packet count exceeds the noise packet hysteresis therefore the AF detection is terminated. By way of at least one embodiment of the invention, although the stable packet count having a value of two is large enough to terminate the AF detection based on the noise packet hysteresis having a value of two, the AF detection may not be terminated until the noise count leads to incrementing the stable packet count.

In the example shown in FIG. 7, in one or more embodiments, the interval count (Intrvl Cnt) starts at 14. On VN events, in at least one embodiment, the counter is decremented. On VS events that conclude a used interval, in one or more embodiments, the counter is incremented. In at least one embodiment, on the last VS event there are enough intervals for AF to check for stability in accordance with FIG. 3. As such, in one or more embodiments, the detection device may find the packet as unstable (AF) (block 180 of FIG. 3), such that the stable packet (block 190 of FIG. 3) is cleared. In at least one embodiment, the noise count may also be cleared in block 170 of FIG. 3.

By way of one or more embodiments, the interval count may not be cleared and, if the next event is VS, the detection device will check for stability again.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A cardiac device configured to detect atrial fibrillation within a heart signal obtained from a heart comprising:
   at least two sensing electrodes;
   at least one input channel that provides an input heart signal;
   a detector that detects sense events (VS) and noise events (VN);
   a noise counter;
   a processor that terminates the detection of atrial fibrillation when the noise counter reaches a predetermined limit;
   at least one noise marker generator that generates further noise events (VN) each at a predetermined time interval after a noise event (VN) has been detected and when the noise event (VN) continues,
       wherein said processor increments and resets the noise counter for each noise event (VN) and each further noise event (VN);
   an interval counter,
       wherein said processor increments, decrements and resets the interval counter; and,
   a stable packet counter,
       wherein said processor increments and decrements the stable packet counter; and,
       wherein for a noise event (VN), the interval counter is decrementable and the noise counter is incrementable, wherein the noise counter and the interval counter are resettable and the stable packet counter is incrementable when the noise counter reaches a predetermined limit, and wherein the detection of atrial fibrillation is terminated when the stable packet counter reaches a predetermined limit.

2. The cardiac device according to claim 1, wherein for a sense event (VS) the interval counter is incrementable for two consecutive sense events (VS), wherein the noise counter and the interval counter are resettable and the stable packet counter is incrementable when the interval counter reaches a defined packet size and meets a stability threshold, and wherein the detection of atrial fibrillation is terminated when the stable packet counter reaches a predetermined limit.

3. The cardiac device according to claim 1, wherein the noise counter and the interval counter are resettable and the stable packet counter is incrementable only when a number of unstable intervals are below a predetermined limit.

4. The cardiac device according to claim 1, wherein a sense event (VS) is detectable for a QRS event in the input heart signal.

5. The cardiac device according to claim 1, wherein the predetermined time interval for incrementing the noise counter due to a continuing noise event includes a range between 0.5 to 4 seconds, or 2 seconds.

6. The cardiac device according to claim 1, wherein the further noise events (VN) are generated only during a programmable duration of time following a detection of atrial fibrillation.

7. The cardiac device according to claim 1, wherein the cardiac device starts detecting atrial fibrillation when one or more of
   the rate of ventricular intervals is above a predetermined rate limit, and
   a predetermined number of ventricular intervals is determined to be not stable;
       wherein a ventricular interval is defined by two consecutive VS events of the input heart signal.

8. A method to detect atrial fibrillation within a heart signal obtained from a heart using a cardiac device, comprising:

providing a cardiac device comprising at least to sensing electrodes, at least one input channel, a detector, a noise counter processor, and at least one noise marker generator;

providing an input heart signal via said at least one input channel;

detecting sense events (VS) and noise events (VN) via said detector;

terminating the detection of atrial fibrillation when the noise counter reaches a predetermined limit via said processor;

generating further noise events (VN) each at a predetermined, time interval after a noise event (VN) has been detected, and when the noise event (VN) continues via said at least one noise marker generator; and, incrementing a noise counter for each noise event (VN) and each further noise event (VN) via said processor; and, wherein said cardiac device further comprises at an interval counter and a stable packet counter, wherein for a noise event (VN) said interval counter is decremented and the noise counter is incremented via said processor, wherein the noise counter and the interval counter are reset and the stable packet counter is incremented when the noise counter reaches a predetermined limit via said processor, and wherein the detection of atrial fibrillation is terminated when the stable packet counter reaches a predetermined limit via said processor.

9. The method according to claim 8, wherein for a sense event (VS) the interval counter is incremented for two consecutive sense events (VS) via said processor, wherein the noise counter and the interval counter are reset and a stable packet counter is incremented via said processor when the interval counter reaches a defined packet sizeand meets a stability threshold, wherein the detection of atrial fibrillation is terminated when the stable packet counter reaches a predetermined limit via said processor.

10. The method according to claim 8, wherein the noise counter and the interval counter are reset and the stable packet is incremented only when a number of unstable intervals are below a predetermined limit.

11. The method according to claim 8, wherein the predetermined time interval for incrementing the noise counter due to a continuing noise event includes a range between 0.5 to 4 seconds, or 2 seconds.

12. The method according to claim 8, wherein the generation of further noise events (VN) is only executed during a programmable duration of time following a detection of atrial fibrillation.

13. The method according to claim 8, wherein the method starts and the cardiac device starts detecting atrial fibrillation when one or more of the rate of ventricular intervals is above a predetermined rate limit, and a predetermined number of ventricular intervals is determined to be not stable;

wherein a ventricular interval is defined by two consecutive VS events of the input heart signal.

* * * * *